United States Patent
House

(10) Patent No.: US 8,177,765 B2
(45) Date of Patent: May 15, 2012

(54) COLLECTION DEVICES FOR CATHETER ASSEMBLIES

(75) Inventor: Jamie Glen House, Colorado Springs, CO (US)

(73) Assignee: Adapta Medical, Inc., Colorado Springs, CO (US)

( * ) Notice: Subject to any disclaimer, the term of this patent is extended or adjusted under 35 U.S.C. 154(b) by 740 days.

(21) Appl. No.: 11/652,524

(22) Filed: Jan. 12, 2007

(65) Prior Publication Data

US 2008/0172016 A1    Jul. 17, 2008

(51) Int. Cl.
*A61M 1/00* (2006.01)

(52) U.S. Cl. .............................. 604/317; 604/327

(58) Field of Classification Search ............ 604/290, 604/317–327, 331, 345, 349–353, 408–415; 222/145.5, 153.01; 137/383; 232/43.1; 206/570
See application file for complete search history.

(56) References Cited

U.S. PATENT DOCUMENTS

| | | | | |
|---|---|---|---|---|
| 4,573,983 A | * | 3/1986 | Annis | 604/322 |
| 4,622,033 A | | 11/1986 | Taniguchi | |
| 4,637,061 A | * | 1/1987 | Riese | 383/38 |
| 4,772,275 A | | 9/1988 | Erlich | |
| 4,834,710 A | | 5/1989 | Fleck | |
| 4,955,879 A | * | 9/1990 | Mervine | 604/327 |
| 5,087,251 A | | 2/1992 | Heyman et al. | |
| 5,147,341 A | | 9/1992 | Starke et al. | |
| 5,149,326 A | | 9/1992 | Woodgrift et al. | |
| 5,181,913 A | | 1/1993 | Erlich | |
| 5,234,420 A | * | 8/1993 | Horton et al. | 604/345 |
| 5,263,947 A | * | 11/1993 | Kay | 604/331 |
| 5,439,456 A | * | 8/1995 | Fabricant | 604/327 |
| 5,643,189 A | * | 7/1997 | Masini | 602/58 |
| 5,725,515 A | | 3/1998 | Propp | |
| 5,779,670 A | | 7/1998 | Bidwell et al. | |
| 5,792,114 A | | 8/1998 | Fiore | |
| 5,895,374 A | | 4/1999 | Rodsten | |
| 6,053,905 A | | 4/2000 | Daignault et al. | |
| 6,059,107 A | | 5/2000 | Nosted et al. | |
| 6,090,075 A | | 7/2000 | House | |
| 6,176,849 B1 | | 1/2001 | Yang et al. | |
| 6,217,569 B1 | | 4/2001 | Fiore | |
| 6,409,717 B1 | | 6/2002 | Israelsson et al. | |
| 6,471,684 B2 | | 10/2002 | Dulak et al. | |
| 6,578,709 B1 | | 6/2003 | Kavanagh et al. | |
| 6,602,244 B2 | | 8/2003 | Kavanagh et al. | |
| 6,634,498 B2 | | 10/2003 | Kayerod et al. | |
| 6,673,053 B2 | | 1/2004 | Wang et al. | |
| 6,736,805 B2 | | 5/2004 | Israelsson et al. | |

(Continued)

OTHER PUBLICATIONS

The Internationa Bureau of WIPO, "International Preliminary Report on Patentability," issued Jul. 14, 2009.

*Primary Examiner* — Tatyana Zalukaeva
*Assistant Examiner* — Benedict L Hanrahan
(74) *Attorney, Agent, or Firm* — Moazzam & Associates, LLC

(57) ABSTRACT

A collection device for a catheter assembly is disclosed providing for an easier catheterization process and fluid collection with the device capable of being folded from a larger form into a smaller, more mobile form. The collection device may have attached to its top portion a connecting tube capable of being stretched and compressed, thereby allowing the user more flexibility and convenience while catheterized. Additionally, the collection device may contain antiseptic agents, fold lines, a drainage tube, fastening mechanisms, and leg strap holders in order to make the device more convenient to use.

7 Claims, 2 Drawing Sheets

U.S. PATENT DOCUMENTS

| | | |
|---|---|---|
| 6,848,574 B1 | 2/2005 | Israelsson et al. |
| 2001/0001443 A1 | 5/2001 | Kayerod et al. |
| 2001/0007060 A1 | 7/2001 | Fiore |
| 2001/0027295 A1 | 10/2001 | Dulak et al. |
| 2001/0027299 A1 | 10/2001 | Yang et al. |
| 2003/0018302 A1 | 1/2003 | Kavanagh et al. |
| 2004/0074794 A1 | 4/2004 | Conway et al. |
| 2004/0153051 A1 | 8/2004 | Israelsson et al. |
| 2004/0256264 A1 | 12/2004 | Israelsson et al. |
| 2005/0015076 A1 | 1/2005 | Giebmeyer et al. |
| 2005/0109648 A1 | 5/2005 | Kerzman et al. |
| 2005/0137582 A1 | 6/2005 | Kull-Osterlin et al. |
| 2006/0025753 A1 | 2/2006 | Kubalak et al. |
| 2008/0154219 A1* | 6/2008 | Longo et al. ............ 604/327 |
| 2008/0262446 A1* | 10/2008 | Ryder et al. ............ 604/317 |

* cited by examiner

COLLECTION DEVICES FOR CATHETER ASSEMBLIES

BACKGROUND OF THE INVENTION

1. Field of the Invention

The present invention relates generally to catheter assemblies. More particularly, the present invention relates to collection devices for catheter assemblies.

2. Background of the Invention

The urinary catheterization procedure is a common medical practice with the procedure being performed today in hospitals, nursing homes, and home settings. When a patient requires a catheter to remain in for a prolonged period of time, an indwelling or Foley catheter is often used. This type of catheter has the benefit of remaining in the bladder for up to one month which decreases the inconvenience of repeated intermittent catheterization. Indwelling urinary catheters are also used in situations where an accurate measurement of urine is required.

There has been a significant increase in highly resistant bacteria within institutions such as hospitals and nursing homes. Every attempt is being taken to decrease infection by destroying the bacteria. Until that is done, however, attempts must be made to decrease a patient's exposure to such potential harmful bacteria.

One common complication of indwelling catheters, as a result of infections often by bacteria, is a Urinary Tract Infection (UTI). There have been many attempts to decrease the incidents of urinary tract infections. A very common trend has been to supply the indwelling catheter pre-attached to a large bedside collection bag. These bedside collection bags are usually of a standard size and can hold up to 2000 mL of urine. The indwelling urinary catheter comes connected to the bedside collection bag to create a "closed system" environment. By not switching from a 2000 mL bedside collection bag to a smaller 500-700 mL leg/day bag, it is hoped that urinary tract infection may be decreased. Every time a urine collection bag is removed from a Foley catheter distal end and replaced with another collection bag, the seal or closed system is broken, and the risk for infection is increased thereby putting the patient at risk.

Conventional urine collection bags have a drain port located somewhere on the bag. Several times throughout the day the nurse or caretaker is required to open the port and drain the urine into a container for discard. Many times in the hospital setting the patient must get out of bed and walk to the bathroom or shower, or the patient may get out of bed for therapy or exercise. This large 2000 mL bedside collection bag becomes a very significant hindrance to mobility and independence.

Because infection may arise during catheterization when a large collection bag is replaced by a smaller one and because it is inconvenient to have a large bag attached to a patient when the patient desires to get out of bed, there is a need in the healthcare industry for a sterile and convenient technique for facilitating the catheterization process and being able to effectively transition between a larger collection bag and a smaller leg/day bag.

SUMMARY OF THE INVENTION

The current techniques for catheterization are inefficient and inconvenient. Infection may arise when an original larger bag is detached, and a smaller leg bag is attached to a distal end of a catheter. The present invention addresses this healthcare problem by providing various devices and techniques to facilitate the catheterization process, and to simplify the transition between a larger collection bag and a smaller leg bag. More specifically, the present invention proposes a foldable collection receptacle with an accordion-like connecting tube, while the collection receptacle is capable of being manipulated between a larger and a smaller form without disconnecting the connecting tube from the collection receptacle.

In one exemplary embodiment, the present invention is a collection assembly. The assembly includes a collection receptacle; an accordion-like connecting tube attached to the top of the collection receptacle; a drainage port located at a bottom of the collection receptacle; a drainage tube; and a holder; wherein the drainage tube is in fluid communication with the drainage port such that the drainage tube can be manipulated in order to control flow of fluid out of the collection receptacle; and wherein the holder is positioned on the collection receptacle such that a tip of the drainage tube may be stored within the holder when no fluid is being drained from the collection receptacle.

In another exemplary embodiment, the present invention is a collection device. The device includes a collection receptacle with fold lines; a drainage port located at a bottom of the collection receptacle; and a holder attached to the collection receptacle; wherein the collection receptacle is initially a larger size which can be folded into a smaller size; wherein the drainage tube is in fluid communication with the drainage port such that the drainage tube can be manipulated in order to control the flow of fluid out of the collection receptacle; and wherein the holder is positioned such that the tip of the drainage tube may be stored within the holder when no fluid is being drained from the collection receptacle.

In certain exemplary embodiments, an accordion-like connecting tube is also included, and is positioned in between the catheter and the collection receptacle. Such accordion-like property allows a long enough tube to reach a side of the bed and the ability to shorten when worn on the leg. Thus, this connecting tube can extend from a few inches, such as about four inches, to several feet, such as about two feet. Other lengths are also possible and within the scope of the present invention.

In certain exemplary embodiments, a clamp on the drainage port or tube, or a screw or other flow-arresting device, is included to prevent flow when such drainage port is not in use.

As used herein and throughout this disclosure, and in order to understand the directional aspects of this invention, "proximal" refers to the section of the device that is closer to the patient's body (e.g., urethra) during catheterization while "distal" refers to the section of the device that is farther away from the patient's body during catheterization.

DETAILED DESCRIPTION OF THE INVENTION

The present invention provides for catheter and catheter assemblies with collection devices such that the operator may more easily transition between a larger collection receptacle and smaller collection receptacle thereby avoiding exposure to infection. In particular embodiments and examples presented herein, such catheters are described with respect to urinary catheterization but it must be noted that such collection devices according to the present invention are not limited to urinary catheters alone but may be applicable to any catheter and catheter assembly that could benefit from the use of such collection devices.

Figure 1:
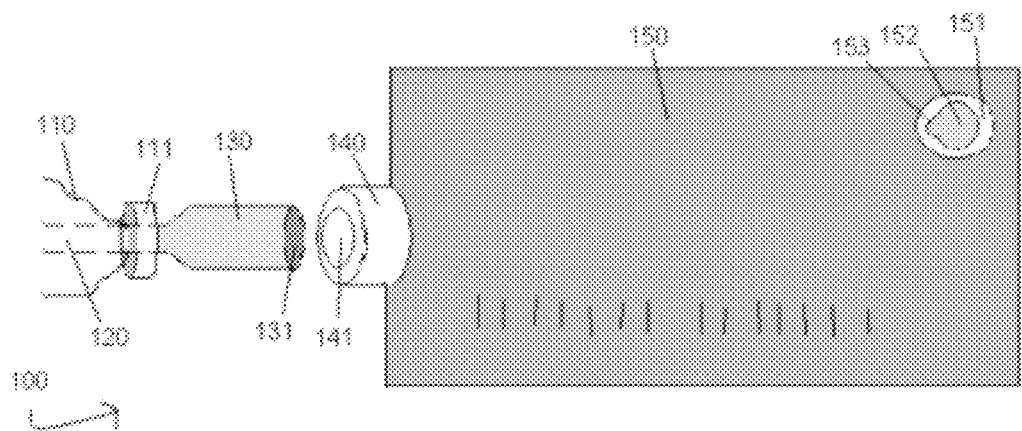
FIG. 1 shows a side view of a reversible catheter assembly which includes a collection receptacle with a drainage port and clamp according to the prior art.

An example of a conventional catheter assembly is shown in FIG. 1 as assembly 100. Assembly 100 includes a collection receptacle 150, a drainage port 151 with a drainage cover 152, a mating collar 140, a catheter distal end 130, a mating stopper 111, a catheter 120, and a sheath 110. The collection receptacle 150 may be of any size such that it is be capable of storing a volume between 300 mL and 5 L of fluid. Other volumes are also possible. The collection receptacle 150 is rectangular in shape as shown in FIG. 1 or it is any other shape including but not limited to a pouch, an oval, a square, or any other geometric shape that would maximize the volume capacity of the collection receptacle while minimizing the bulkiness of the collection receptacle. The collection receptacle 150 contains a drainage port 151 as shown in FIG. 1.

The drainage port 151 is circular in shape or it is any other shape including but not limited to an oval, a square, or any other geometric shape that would allow for a desired rate of volume flow (e.g., fast or slow) out of the collection receptacle 150 in order to either empty the collection receptacle fully or partially (e.g., to obtain a urine sample). The drainage port 151 is of a size such that it allows for a desired rate of volume flow out of the collection receptacle 150 in order to either empty the collection receptacle fully or partially. The drainage port 151 is located at the distal end (the bottom) of the collection receptacle 150 as shown in FIG. 1 such that it is in a position to efficiently and optimally drain the contents of the collection receptacle 150 when the receptacle is filled with urine.

Assembly 100 also includes a drainage cover 152 covering the drainage port 151. The drainage cover 152 is of any shape as described above for the drainage port 151 as long as the drainage cover 152 is able to effectively occlude the drainage port 151 when the drainage cover 152 is closed (e.g., mated with the drainage port) thereby preventing any leakage out of the collection receptacle 150. The drainage port 151 is attached to the collection receptacle 150 via any appropriate technique such that when the drainage cover 152 is open (e.g., not mated with the drainage port 151), the drainage cover remains attached to the collection receptacle thereby preventing the operator from misplacing or losing the drainage cover 152 and also allowing the operator to easily close the drainage cover after the desired amount of urine is drained from the collection receptacle 150. The drainage cover 152 also possesses a grippable tab 153 that is used to open and close the drainage cover.

Before catheterization, the mating stopper 111 is mated with the mating collar 140 so that the catheter distal end 130 is situated within the collection receptacle 150. In this way, the urine outlet 131 is positioned within the collection receptacle 150 before the urine is drained into the receptacle. The connection provided by the mating of the stopper and collar is strong enough to effectively resist undesired disconnection before, during, and after the desired amount of fluid is extracted from the patient. After the desired amount of fluid is extracted and/or the catheterization process is completed, the operator may exert sufficient force to disconnect the mating stopper 111 from the mating collar 140 thereby possibly separating the collection receptacle 150 from the catheter distal end 130. The operator then places the collection receptacle 150 over a specimen bottle or a toilet, and then grasps the grippable tab 153 with one hand and removes the drainage cover 152 from the drainage port 151 thereby allowing the collected urine to flow out of the collection receptacle by way of gravity. Once the desired amount of drained fluid is released (e.g., a sample size or the whole volume of collected fluid) from the collection receptacle, the operator replaces the drainage cover 152 so that it mates with the drainage port 151. To close the drainage cover 152, the user mates the drainage cover 152 with the drainage port 151 (e.g., including but not limited to snapping the cover into the port) firmly enough to provide a leak-free seal between the drainage cover and the port.

Figure 2:
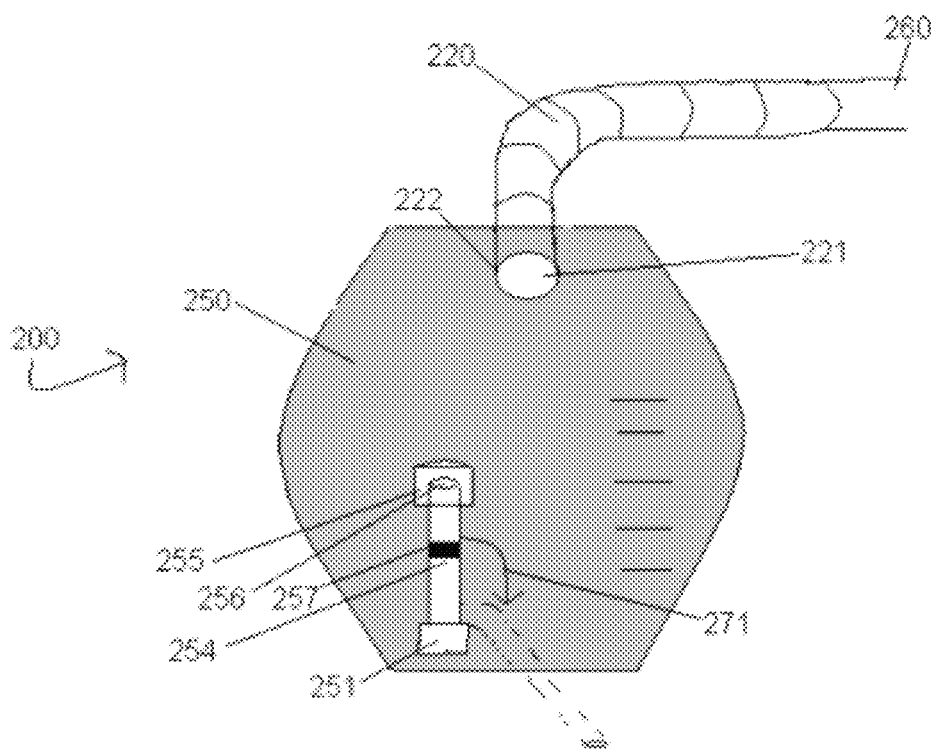
FIG. 2 shows a front view of a catheter assembly with a collection receptacle which possesses an accordion-like connecting tube, a drainage port, and a drainage tube with an optional clamp according to an exemplary embodiment of the present invention.

An exemplary embodiment of the present invention incorporated into a catheter assembly 200 is shown in FIG. 2, and includes a collection receptacle 250, a drainage port 251 with a drainage tube 254, a clamp 257, a holder 255, and a connecting tube 220. The collection receptacle 250 may be pouch shaped as shown in FIG. 2 or it may be any shape including but not limited to a rectangle, oval, square, or any other geometric shape such that the volume capacity of the collection receptacle may be maximized while the bulkiness of the collection receptacle may be minimized. The collection receptacle 250 may be of any size or size range, including but not limited to between 300 mL and 5 L. The collection receptacle 250 may contain an antiseptic pellet (not shown) capable of maintaining an internal sterile environment for the collection receptacle. The antiseptic pellet may be a free pellet or it may be "cage" ball pellet capable of releasing its antiseptic agent in a time sensitive fashion. This "cage" ball may be capable of releasing the antiseptic agent constantly over a defined time period (e.g., 1-2 months). Such a time-released pellet may keep the collection receptacle 250 and assembly 200 free of contamination.

The connecting tube 220 may act as a sterile fluid conduit by allowing a sterile passageway for fluid to drain into the collection receptacle 250 from a catheter (not shown) connected at attachment site 260. The connecting tube 220 may contain on its inner surface any antiseptic agent (not shown) capable of maintaining a sterile environment inside its surface and therefore inside assembly 200. The antiseptic agent may effectively prevent contamination and subsequent patient infection arising from bacteria. The connecting tube 220 may be comprised of any suitable material such that the tube can act like an accordion and be capable of stretching to a length of approximately 4 feet and be capable of compressing to a length of approximately 1 foot or less when so manipulated. The material property that allows such flexibility in length for the connecting tube is similar to that of a bendable plastic straw. The longer length of the connecting tube may be suitably used when the collection receptacle is larger (e.g., 2-5 L) thereby providing maximum length from the patient to the collection receptacle, and a maximum volume for fluid collection (e.g., for when the patient is lying in bed). Alternatively, the shorter length of the connecting tube may be suitably used when the collection receptacle is smaller (e.g., 300 mL) thereby providing a more manageable length from the patient to the collection receptacle, and a more convenient collection receptacle size (e.g., for when the patient is mobile). The connecting tube 220 may be permanently attached to the urine inlet 221 at attachment site 222 via any suitable permanent attachment means known in the catheter art (e.g., heat sealing, clamping, etc.). In this way, a sterile environment may be maintained within catheter assembly 200. The connecting tube 220 may also be attached permanently to a catheter (not shown) at the proximal end 260 of assembly 200 as described above.

The drainage port 251 may be situated as shown in FIG. 2 at the bottom of the collection receptacle so as to maximize the usability and drainability of the collection receptacle. The drainage port 251 may be rectangular in shape as shown in FIG. 2 or it may be any other shape such that the port can effectively and efficiently allow the passage of fluid out of the collection receptacle at a desired rate. Additionally, the drainage port 251 may be of any size. The drainage port 251 may also contain a drainage tube 254 which may effectively provide a conduit for the urine to drain out of the collection receptacle 250. A base portion of the drainage tube 254 may be attached to and sealed with the drainage port 251 via any attachment method including, but not limited to, heat sealing in order to prevent leakage. The attachment method may allow the drainage tube 254 to be in fluid communication with the drainage port 251 such that the urine may flow out of the collection receptacle and into the drainage tube when the tube is removed from the holder 255 and pointed downward as shown by arrow 271. The attachment method at urine inlet 221 between the collection receptacle and connecting tube and the attachment of the drainage tube 254 with the drainage port 251 may be such that during urine flow, no urine is able to leak through and thus a leak free seal may be maintained between at the urine inlet 221 and the drainage port 251. An optional clamp 257 may also be present on the drainage tube 254 to further prevent premature fluid leakage and to allow the user more control over the urine flow. The clamp 257 may encompass the drainage tube 254 and may be comprised of any material and may be formed in any shape such that the clamp is capable of effectively allowing fluid to pass through the drainage tube when it is in an open position, and then capable of occluding the drainage tube when it is in a closed position (e.g., not allowing fluid to pass).

At any point during the catheterization, the operator may remove the drainage tube 254 from within the holder 255 thereby exposing the drainage outlet 256. The drainage tube may be pulled out of the holder 255 just prior to catheterization. The drainage tube 254 may be manipulated by the user to adjust the amount and flow rate of urine allowed to pass through the drainage tube 254. In order to detach the drainage tube 254 from the holder 255 and therefore drain the collection receptacle 250, the operator may grasp the drainage tube anywhere along its body and pull down as shown by arrow 271. This motion may allow the user to bend the drainage tube 254 towards the ground to control urine flow.

For example, the operator may grasp the drainage tube 254 with one hand by forming a fist around the tube. After pulling down, the operator may rotate his or her wrist away from the collection receptacle to expose the drainage outlet 256. By varying the magnitude of the twist, the operator may control the flow rate of urine out of the collection receptacle 250. To stop the flow of urine out of the collection receptacle 250, the operator may grasp the drainage tube as specified above and may manipulate the drainage tube 254 to an almost horizontal position (e.g., parallel to the floor) or the user may engage the clamp 257. The operator may then insert the drainage outlet 256 and proximal portion of the drainage tube 254 back into the holder 255.

In order to achieve all of these functions and limitations, the collection receptacle 250 may be flexible and not easily broken or ripped, and the drainage tube 254 may also be flexible and capable of manipulation. The holder 255 may also be flexible and may be attached to the collection receptacle 250 via any attachment means including but not limited to adhesion. The holder 255 may be attached to the collection receptacle at a location such that the drainage tube 254 is able to rest within the holder as shown in FIG. 2. Thus, the distance between the holder 255 and the drainage port 251 must be roughly equivalent to the length of the drainage tube in order for the drainage tube 254 to rest within the holder 255 without any support from the operator.

Figure 3A:
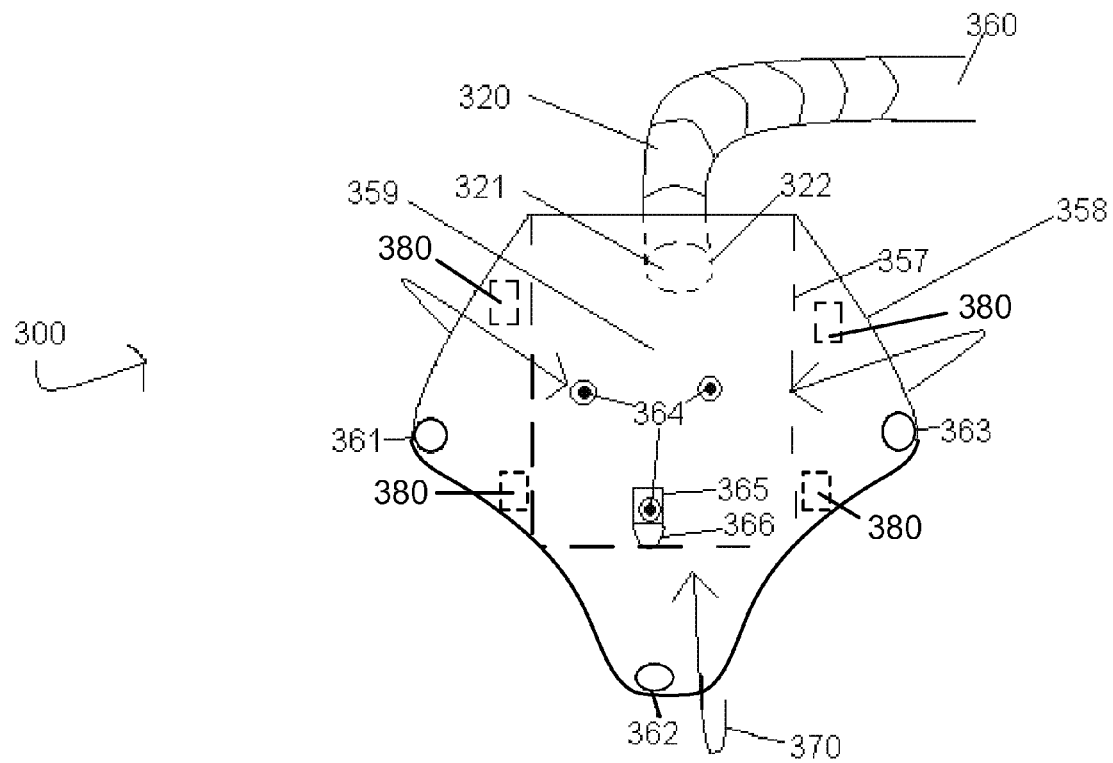
FIG. 3A shows a front view of a catheter assembly with a foldable collection receptacle which possesses an accordion-like connecting tube, a drainage port, a drainage tube, and fasteners according to an exemplary embodiment of the present invention.
Figure 3B:
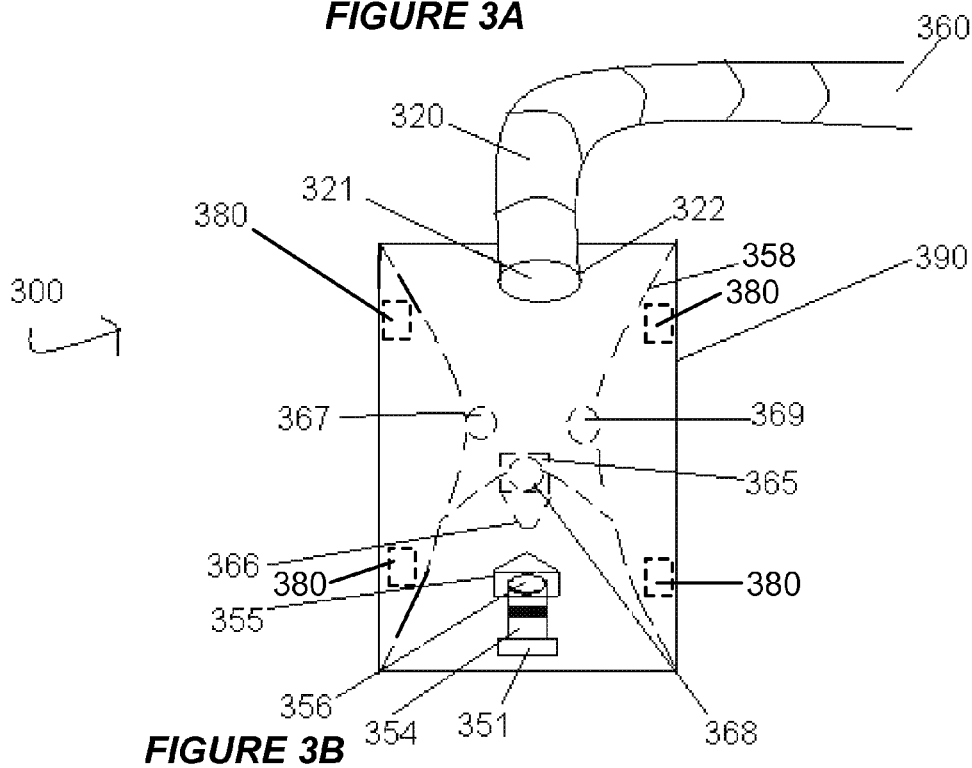
FIG. 3B shows a rear view of the catheter assembly in FIG. 3A but is in the smaller folded position according to an exemplary embodiment of the present invention.

Yet another exemplary embodiment of the present invention incorporated into a catheter assembly 300 is shown in FIG. 3A, and includes an unfolded collection receptacle 358 with fold lines 357, left fastener 361, bottom fastener 362, right fastener 363, receiving bodies 364, drainage port 351, drainage tube 354, holder 355, connecting tube 320, pull attachment 365, and pull ring 366. The unfolded collection receptacle 358 as shown in FIG. 3A may be of any size such that it is capable of receiving and storing up to 5 L of fluid. The receptacle may have fold lines 357 on its surface as shown in FIG. 3A such that the unfolded collection receptacle 358 is capable of being folded (e.g., reduced from a size capable of holding up to 5 L of fluid to a smaller size capable of holding less than 5 L of fluid). The fold lines 357 are shown as residing on the same side as the drainage port 351 and drainage tube 354 but this is not a limiting characteristic for this exemplary embodiment and they may be on the other side or on both sides of the collection receptacle. The fold lines 357 may be situated such that the operator is able to fold both sides of the receptacle along with the bottom of the receptacle in the direction shown by arrows 370 while avoiding interfering with the integrity of the drainage port 351 and the drainage tube 354. For example, the operator may fold the left side of the receptacle toward the middle of the front side of the receptacle such that the left fastener 361 is brought closer to approximately the center of the front side (e.g., the side opposite the drainage port 351 and tube 354) and is made to mate with the left receiving body 364. Then, the operator may fold the right side of the receptacle toward the middle of the front side of the receptacle such that the right fastener 363 is brought closer to approximately the center of the front of the receptacle and is made to mate with the right receiving body 364. Finally, the operator may fold the bottom of the receptacle toward the middle of the receptacle such that the bottom fastener 362 is brought closer to approximately the center of the front side of the receptacle and is made to mate with the bottom receiving body 364. After all the fasteners are mated with the receiving bodies, the smaller, more mobile folded collection receptacle 390 is formed as shown in FIG. 3B. The leg strap holders 380 may be on the same side as the drainage port 351 as shown in FIG. 3A but they may be on the left, right, and bottom flaps of the collection receptacle. Thus, after the smaller collection receptacle is formed (e.g., the flaps are folded over), the leg strap holders 380 are now on the front side of the collection receptacle as shown in FIG. 3B and do not interfere with the user's operation of the drainage port 351 and tube 354. After the folded collection receptacle 390 is formed, the leg strap holders 380 are ready for the leg straps (not shown) to be attached. This sequence of steps as described above does not have to be strictly followed and the right side or the bottom may be folded first, for example.

The fasteners described above may consist of snapping protrusions that mate with receiving bodies 364 on the front side of the collection receptacle. Once mated, the fasteners and receiving bodies form the mated bodies 367, 368, and 369 as shown in FIG. 3B. Alternatively, the fasteners may mate with each other. Such a snapping material for the fasteners may be composed of plastic but is not limited to such material. The fasteners may alternatively be composed of magnetic, hook and loop mechanism (such as VELCRO), or other materials that may be reversibly attached to the collection receptacle or to each other so long as the material is able to securely and reversibly bind to the surface of the collection receptacle or to each other. The adhesive force provided via the connection of the fasteners to each other or to the receptacle may be strong enough so as to avoid premature disconnection, but not so strong as to make it difficult for the operator to achieve the desired disconnection.

Alternatively, a mating plastic zipper-like locking mechanism may be used to seal off different chambers within the unfolded collection receptacle 358 by gently pressing down on the mating plastic zipper components strategically placed along folding lines 357 throughout the unfolded collection receptacle 358. In such a manner, a user may choose one or more chambers within the unfolded collection receptacle 358 that may be used to collect urine. For example, a user may wish to seal off the two side chambers separated by the two vertical plastic zipper lines places at the folding lines 357. In such a scenario, urine will only be collected in the center two chambers, center top chamber 359 and the chamber directly below it in the figure. A user may even wish to exclude the lower center chamber as well by pressing and locking the zipper mechanism horizontally separating the center top chamber 359 and the center lower chamber. In one exemplary embodiment, a U-shaped continuous zipping mechanism may be used to separate one or more chambers.

With each closing off of a chamber within the collection receptacle, the volume able to receive and store urine is decreased, thus making smaller urine volume measurements easier and more accurate. A gradated visual measurement scale may also be included on the surface of the receptacle (not shown) so that the user may determine the exact volume of urine collected depending on which chambers are being used and which have been excluded by the plastic zipper locking mechanism. Such mechanism may be, for example, similar to one used conventionally in plastic sandwich bags. Because such plastic zipper locking mechanism is reversible, a user may choose to open up a sealed and excluded chamber to allow it to also be used to collect and house urine.

The center top chamber 359 may be opened and closed via pull ring 366. The pull ring 366 may be attached to the center top chamber 359 via a pull attachment 365. The pull ring 366 may be of any shape and configuration such that the user is able to grasp it and pull the sealed portion of the collection receptacle corresponding to the center top chamber 359 sufficiently to release the bound fold lines 357 (e.g., bound in any manner as described above). In this way, the user is able to easily manipulate the size of the collection receptacle from small to large and vice versa. The user may form and undo formed chambers simply by pulling at the opposite sides of the receptacle at the folding lines 357 which separate a used versus unused chamber, thereby allowing urine to flow into that chamber as well.

The folded embodiment of the present invention is shown in FIG. 3B and is labeled as the folded collection receptacle 390. The size of the folded collection receptacle 390 (e.g., 300 mL to 1000 mL) may be smaller than the size of the unfolded collection receptacle 358 (e.g., up to 5 L). The ability to convert the unfolded collection receptacle 358 into the folded collection receptacle 390 enables a patient to increase his or her mobility since a larger receptacle (e.g., the unfolded collection receptacle 358) is typically used for when the patient is in bed while a smaller, and more easily transportable receptacle (e.g., the folded collection receptacle 390) is typically used for when the patient is out of bed and walking around. Thus, this exemplary embodiment of the present invention may have particular advantages for the use of Foley catheters, or indwelling catheters, wherein the unfolded collection receptacle 358 may be used for the patient while he or she is in bed, and the receptacle can then be folded into the folded collection receptacle 390 if and when the patient desires to get out of bed but does not wish to disconnect the catheter or the collection receptacle.

In order to increase the convenience and portability of the folded collection receptacle 390, the receptacle may contain leg strap holders 380 as shown in FIGS. 3A and 3B and as described above. These straps may be situated such that they do not interfere with the drainage port 351 and drainage tube 354 when the collection receptacle is in the folded form. In this way, the front side of the receptacle may be attached to the patient's leg while the back side of the receptacle, which contains the drainage port and tube, may be available for the operator to manipulate. The drainage tube 354 may also be attached to the bottom of the receptacle when the receptacle is in the folded form as shown in FIG. 3B. The leg strap holders 380 may be attached to the receptacle via any method commonly used and known to one of ordinary skill in the catheter arts (e.g., heat sealing, adhesion, etc.) and the leg strap holders 380 may be made from the same material as the collection bag, or cloth material with VELCRO or rubber, for example, so that they may be reliably and reversibly secured around the leg of the patient.

drainage port 351, the drainage tube 354, and the holder 355 may effectively serve the same functions and be capable of performing the same operations while being subject to the same parameters as described above in assembly 200 (e.g., drainage port 351 may be use to empty the collection receptacle 350 using the drainage tube 354, etc.). Additionally, the inner surface of the connecting tube 320 may be coated with an antiseptic agent as described above to prevent contamination. Also, the collection receptacles as described in assembly 300 (e.g., both the unfolded and the folded collection receptacles) may contain an antiseptic pellet in order to maintain sterility as described. Finally, a catheter may be attached at attachment site 360 as described above.

All of the materials used for the present invention may be comprised of artificial or naturally occurring non-degradable biocompatible polymer or rubber compounds such that the materials used for the present invention serve the functions delineated in this application. Such compounds can include, but are not limited to, polyester based biocompatible polymers, nylon-based biocompatible polymers, latex based biocompatible polymers, Teflon, polytetrafluoroethylene (PTFE) polymers, polyvinyl chloride (PVC) polymers, silicone polymers, polyurethane polymers, silicone polyurethane polymers, ethylene-vinyl acetate copolymers, polyethylene polymers, and thermoplastic polymers.

The manufacturing methods that can be employed for the present invention include, but are not limited to, conventional techniques used in the industry to produce similar function products, as apparent to one having ordinary skill in the art.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A fluid collection device, the device comprising:
    a collection receptacle having a plurality of receiving bodies including a drainage port and a urine inlet adapted to receive fluid from a urinary catheter;
    a fold line including a plastic zipper seal to reversibly separate the collection receptacle into a plurality of sealed chambers;
    wherein the collection receptacle is capable of being reversibly sealed along the fold line using the plastic zipper seal resulting in a smaller collection receptacle having a decreased volume of no more than one-fifth of a volume of the collection receptacle, the collection receptacle including a graduated visual measurement scale such that the user may use the graduated visual measurement scale to determine a volume of urine in the collection receptacle and the smaller collection receptacle;
    a fastener on each sealed chamber to reversibly mate with one of the plurality of receiving bodies thereby maintaining the decreased volume of the smaller collection receptacle; and
    wherein the drainage port and urine inlet are located on the smaller collection receptacle.

2. The collection device of claim 1, wherein the collection receptacle is capable of receiving and storing up to about 5 L of fluid.

3. The collection device of claim 1, wherein the smaller collection receptacle is capable of storing between 300 mL and 500 mL of fluid.

4. The collection device of claim 1, further comprising a connecting tube attached to the urine inlet of the collection receptacle wherein the connecting tube can be stretched to about 4 feet and compressed to about 4 inches.

5. The collection device of claim 1, further comprising an antiseptic coating on an inner surface of the collection receptacle to prevent contamination and maintain sterility.

6. The collection device of claim 1, further comprising an antiseptic pellet within the collection receptacle to maintain sterility.

7. The collection device of claim 1, wherein the outside of the center of the smaller collection receptacle has a pull ring by which a user can grasp and pull the pull ring to release the sealed fold lines to manipulate the collection receptacle from the smaller collection receptacle to the collection receptacle.

* * * * *